US00PP36118P2

(12) United States Plant Patent
Dirr et al.

(10) Patent No.: US PP36,118 P2
(45) Date of Patent: Sep. 17, 2024

(54) ***HYDRANGEA* PLANT NAMED 'Bailpantwo'**

(50) Latin Name: *Hydrangea paniculata*
Varietal Denomination: Bailpantwo

(71) Applicant: Bailey Nurseries Inc., Newport, MN (US)

(72) Inventors: Michael A. Dirr, Bogart, GA (US); Jeff Beasley, Lavonia, GA (US); Mark Griffith, Watkinsville, GA (US); Rhonda Helvick, Madison, GA (US); Oren McBee, Bishop, GA (US); David Jonathan Roberts, Athens, GA (US); Justin Schulze, Athens, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 18/528,120

(22) Filed: Dec. 4, 2023

Related U.S. Application Data

(60) Provisional application No. 63/434,288, filed on Dec. 21, 2022.

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea paniculata* plant named 'Bailpantwo' that is characterized by its compact plant habit (reaching 1.2 to 1.5 m in height and spread), its mid to late blooming season in Minnesota, its panicles that open creamy white in color and age to a dark pinkish red in color, its dense branching, and its floriferous blooming habit.

1 Drawing Sheet

Botanical classification: *Hydrangea paniculata.*
Varietal denomination: *'Bailpantwo'.*

BACKGROUND OF THE INVENTION

The present invention relates to a new and distinct cultivar of *Hydrangea paniculata* and will be referred to hereafter by its cultivar name, 'Bailpantwo'. 'Bailpantwo' represents a new panicle hydrangea, a perennial shrub grown for use as a landscape plant.

'Bailpantwo' was derived from an ongoing breeding program conducted by the Inventors in Watkinsville, Georgia. The goals of the breeding program are to develop new cultivars of *Hydrangea paniculata* with compact plant habits, floriferous blooming habits, and tolerance to heat in southern climates.

'Bailpantwo' originated as a seedling that arose from seed planted from open pollination of *Hydrangea paniculata* 'PIIHP-I' (U.S. Plant Pat. No. 23,387) in summer of 2012. The male parent is therefore unknown. 'Bailpantwo' was selected as a single unique plant in summer of 2013 from the resulting seedlings.

Asexual propagation of the new cultivar was first accomplished by softwood stem cuttings by one of the Inventors in Watkinsville, Georgia in summer of 2014. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailpantwo' as a unique cultivar of *Hydrangea.*

1. 'Bailpantwo' exhibits a compact plant habit (reaching 1.2 to 1.5 m in height and spread).
2. 'Bailpantwo' exhibits mid to late blooming season in Minnesota.
3. 'Bailpantwo' exhibits panicles that open creamy white in color and age to a dark pinkish red in color.
4. 'Bailpantwo' exhibits dense branching.
5. 'Bailpantwo' exhibits a floriferous blooming habit.

The parent plant of 'Bailpantwo' differs from 'Bailpantwo' in having a later blooming period (2 to 3 weeks later in Minnesota), flowers that age to a light, blush pink color, and inflorescences with a greater density of sterile florets. 'Bailpantwo' can be most closely compared to the *Hydrangea paniculata* cultivars 'Rensun' (U.S. Plant Pat. No. 25,438) and 'Rendia' (U.S. Plant Pat. No. 24,667). 'Rensun' is similar to 'Bailpantwo' in having a compact and rounded plant habit and full panicles. 'Rensun' differs from 'Bailpantwo' in having inflorescences with white flowers that age to medium pink in color, an earlier blooming period (3 to 4 weeks earlier in Minnesota), and a plant habit that is less dense with weaker stems. 'Rendia' is similar to 'Bailpantwo' in having a compact plant habit and inflorescences that age to a dark pinkish red color. 'Rendia' differs from 'Bailpantwo' in having an earlier blooming habit (1 to 2 weeks earlier in Minneosta), a more open plant habit with weaker stems, and inflorescences with fewer sterile flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include a website listing by Nature Hills, Home and Garden Fullfillment, Garden Centerpoint, and My WAHM Plan.

BRIEF DESCRIPTION OF THE DRAWING

The accompanying color photograph illustrates the overall appearance and distinct characteristics of the new *Hydrangea.*

The photograph was taken of a two-year-old plant of 'Bailpantwo' as grown outdoors in a trial bed in Cottage Grove, Minnesota. The colors in the photograph are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'Bailpantwo' as grown outdoors in a trial bed in Cottage Grove, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Mid to late summer to frost in Minnesota.

*Plant type.*—Deciduous shrub, panicle type *Hydrangea.*

*Plant habit.*—Compact, densely branched.

*Height and spread.*—Reaches about 1.5 m in height and spread as a mature plant in the landscape.

*Cold hardiness.*—At least in U.S.D.A. Zone 4.

*Diseases and pests.*—No susceptibility and resistance to diseases or pests has been observed.

*Root description.*—Fine, fibrous and dense, 164B in color.

*Propagation.*—Softwood stem cuttings.

*Root development.*—An average of 3 weeks for root initiation with a young rooted plant produced in an average of 12 weeks (in summer).

*Growth rate and vigor.*—Moderate.

Branch description:

*Branch shape.*—Rounded.

*Branch strength.*—Strong.

*Branch color.*—Young; 145A (with flocci rubbed off), mature; 143B (with flocci rubbed off), old branches; 200B and 162A, trunk; striations of 200A, 202D, and 196D.

*Branch size.*—Main; average of 30 cm in length and 1 cm in diameter, lateral; 25 cm in length and 5 mm in diameter.

*Branch surface.*—Young; slightly glossy, densely covered with short, soft tangled floccose pubescence, 145B in color, mature; slightly glossy, densely covered with short, soft tangled floccose pubescence, color; 145C, moderately flushed with 183A, also sparsely covered with round shaped lenticels, an average of 1 mm in diameter, 159C in color, old stems, rugose, glossy, wood; rugose, matte and exfoliating.

*Branch aspect.*—Upright to slightly outward.

*Internode length.*—An average of 6 cm.

*Branching.*—Moderately branched, main; 4, lateral; 4.

Foliage description:

*Leaf shape.*—Ovate.

*Leaf arrangement.*—Opposite.

*Leaf division.*—Simple.

*Leaf base.*—Rounded.

*Leaf apex.*—Apiculate.

*Leaf margins.*—Serrate.

*Leaf blade lobing.*—Absent.

*Leaf venation.*—Pinnate, color; upper surface translucent, lower surface 193A.

*Leaf size.*—An average of 8 cm in length and 5 cm in width.

*Leaf attachment.*—Petiolate.

*Leaf number.*—An average of 12 (6 pairs) per lateral stem.

*Leaf surface.*—Young and mature upper and lower surface; matte, mature upper surface densely covered with tiny, stiff pilose pubescence, 155D in color, 0.3 mm in length barely distinguishable.

*Leaf color.*—Young and mature upper surface 141A, young and mature lower surface; 138A.

*Petioles.*—An average of 8 mm in length and 2 mm in width, flattened, top side cupped, both surfaces slightly glossy, densely covered with short, soft tangled floccose pubescence, color; upper surface 145A, flushed with 183A, lower surface 145D.

Inflorescence description:

*Inflorescence type.*—Terminal conical panicle, comprised of single sterile flowers and fertile flowers, fertile flowers.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 12 cm in height and 14 cm in diameter.

*Flower number.*—An average of 25 sterile flowers and 150 fertile flowers per panicle.

*Flower fragrance.*—None.

*Flower aspect.*—Sterile flowers; upright, drooping when fading, fertile flowers; held upright to outward from peduncle.

*Flower size.*—Sterile flowers; (including showy sepals) up to 3 cm in diameter and 4 mm in depth, fertile flowers; an average of 1 cm in diameter and 5 mm in depth.

*Flower type.*—Rotate.

*Peduncles.*—Primary peduncles; strong, flattened oval in shape, an average of 2.5 cm in length and 3 mm in width, secondary peduncles 2 cm in length and 2 mm in width, 142C in color, peduncle surfaces slightly sheen, densely covered with short, soft tangled floccose pubescence.

*Pedicels.*—Sterile flowers; moderate strength, an average of 2 cm in length and 1 mm in width, 155A in color, surface is matte and glabrous, fertile flowers;

moderate strength, an average of 3 mm in length and 1 mm in width, 155A in color, surface is matte and glabrous.

*Petals.*—Sterile flowers: petal spot (flower bud); 1 mm in depth and diameter, round in shape, color; when young 157D, tip lightly flushed with 48A, when petals open; average of 4, deeply concave in shape, acute apex, cuneate base, entire margins, average of 2 mm in length, 1 mm in width, both surfaces are glabrous and matte, color: both surfaces when opening and fully open NN155C, fall colors; petals typically drop after full maturity, fertile flowers; petal spot (flower bud); 1 mm in depth and diameter, round in shape, color; when young 145A, mature 157D, when petals open; average of 5, rotate, concave in shape, acute apex, cuneate base, entire margins, 3 mm in length and 2 mm in width, both surfaces are glabrous, satiny, and matte, color: both surfaces when opening and fully open NN155C, fall colors; petals drop after maturity.

*Sepals.*—Sterile flowers; 4, rotate, broadly obovate in shape, apex is un-deeply emarginate to obtuse, base is cuneate, entire margins, 1.5 cm in length, 1.3 cm in width, both surfaces glabrous, satiny, and matte, color: after bud burst upper surface; 144C, after bud burst lower surface; N144D, when opening upper surface; 150C to 150D, light flushes of 149A, when opening lower surface; 149D, center NN155C, light flushes of 149C, fully open upper and lower surface; 157B, sometimes lightly flushed with 150C and 150D, mature and fading; both surfaces change to 145A, becoming flushed and changing to 63B, fall colors; upper and lower surface a blend of 142B, 157A, 158C, heavily flushed around edges and veins with 71A, as the sepals fade becoming 71A, fertile flowers; average of 5, fused, 10% of top portion free, acute apex, broadly cuneate base, entire margins, 0.9 mm in length, 0.8 mm in width, surfaces are matte and glabrous, young sepals both surfaces; 193A in color, mature and fading both surfaces; 144B, becoming flushed with 63B.

Reproductive organs:

*Gynoecium.*—Sterile flowers; 1 pistil, an average of 2 mm in length, fine, stigma; very small and fine, 0.3 mm in length, NN155C in color, style; 1 mm in length, NN155C in color, ovary is superior, 1 mm in depth, NN155C in color, fertile flowers; 3 pistils, an average of 1 mm in length, stigma; club-shaped and 155C in color, style; 0.75 mm in length, 157D in color, ovary is superior, 3 mm in depth, 1 mm in diameter, 158B in color.

*Androecium.*—Sterile flowers; 8 stamens, filaments; an average of 2 mm in length and NN155C in color, anthers; broad oblong in shape, an average of 0.5 mm in width, 0.3 in depth, N200A in color, pollen; not observed, fertile flowers; 8 to 10 stamens, filaments; an average of 4 mm in length and NN155C in color, anthers; broad oblong in shape, an average of 0.7 mm in width, 0.5 in depth, 163*C in color, fading to* 200A and 158D in color, pollen; moderate, 158D in color.

*Fruit and seed.*—Fertile flowers produce a small fruit with no seeds; 2 mm in length, 1 mm in width, glossy surface, 144A in color.

It is claimed:

1. A new and distinct cultivar of *Hydrangea* plant named 'Bailpantwo' substantially as herein illustrated and described.

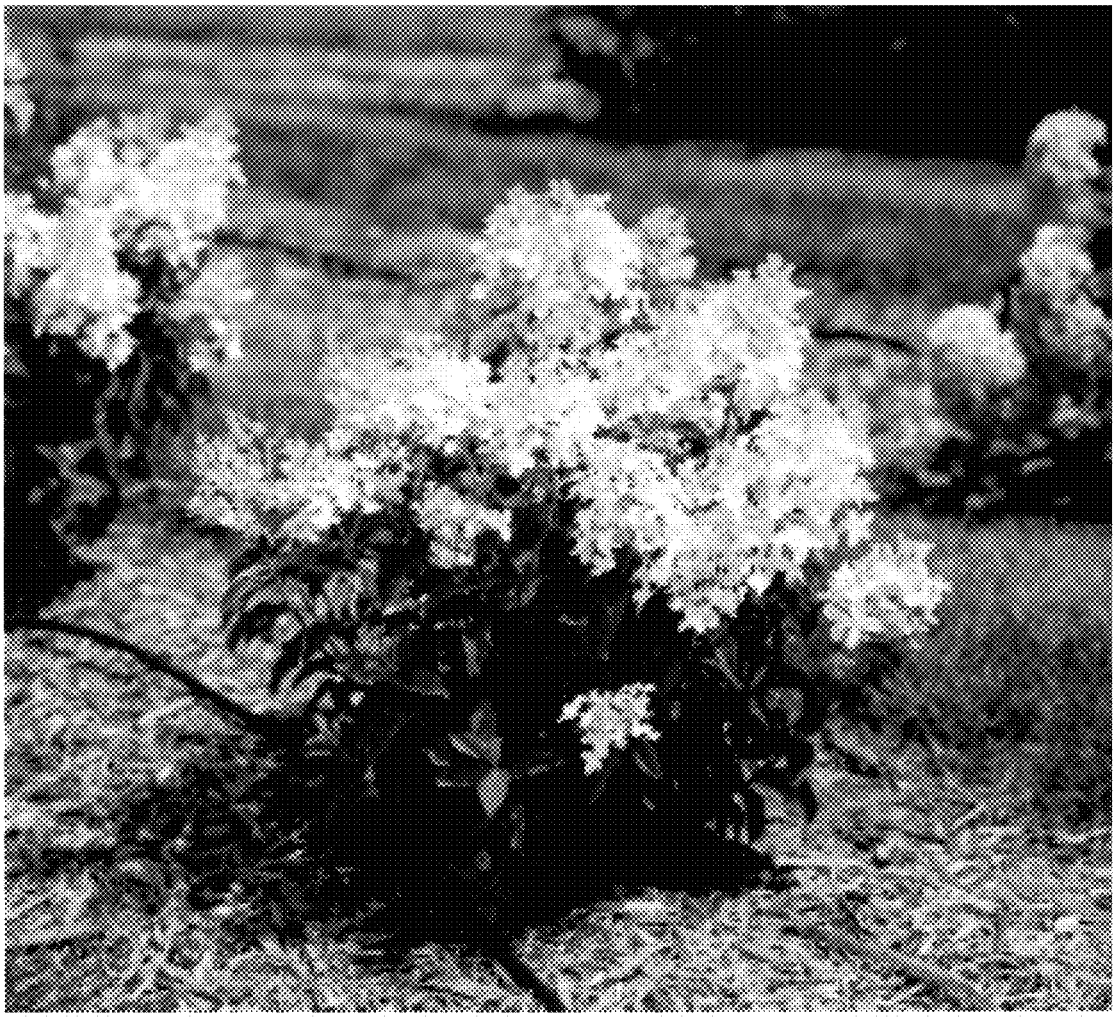

* * * * *